US006551253B2

(12) United States Patent
Worm et al.

(10) Patent No.: US 6,551,253 B2
(45) Date of Patent: *Apr. 22, 2003

(54) INCISIONAL BREAST BIOPSY DEVICE

(75) Inventors: Dustin Worm, Delton, MI (US);
Martin Flatland, Kalamazoo, MI (US);
Mark Tomandl, Hastings, MI (US);
Mark A. Penrod, Delton, MI (US);
Warren D. Lun, Battle Creek, MI (US)

(73) Assignee: Imagyn Medical Technologies, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,444

(22) Filed: Feb. 2, 2001

(65) Prior Publication Data
US 2001/0014778 A1 Aug. 16, 2001

Related U.S. Application Data

(63) Continuation-in-part of application No. 09/692,928, filed on Oct. 20, 2000, now Pat. No. 6,383,145, which is a continuation-in-part of application No. 09/542,623, filed on Apr. 4, 2000, now Pat. No. 6,267,732, which is a continuation of application No. 09/151,439, filed on Sep. 11, 1998, now Pat. No. 6,080,113.
(60) Provisional application No. 60/058,691, filed on Sep. 12, 1997.

(30) Foreign Application Priority Data

Sep. 14, 1998 (US) ................. PCT/US98/18172

(51) Int. Cl.$^7$ ............................................. A61B 10/00
(52) U.S. Cl. ..................... 600/564; 600/567; 606/170
(58) Field of Search ................................. 600/562, 564, 600/566, 567, 568; 604/22, 164.01, 164.11–165.1, 170.01–170.02; 606/130, 167, 170, 180

(56) References Cited

U.S. PATENT DOCUMENTS

| 254,154 A | 2/1882 | Preston | 411/224 |
| 417,797 A | 12/1889 | Van Fleet | 84/95.1 |

(List continued on next page.)

FOREIGN PATENT DOCUMENTS

| EP | 0761170 | 12/1997 |
| GB | 0653191 | 5/1995 |
| WO | 8201988 | 6/1982 |
| WO | 9724070 | 7/1997 |

Primary Examiner—Charles A. Marmor, II
(74) Attorney, Agent, or Firm—Howard & Howard

(57) ABSTRACT

A biopsy device is provided which includes a localization needle having a guide wire preloaded into the biopsy device. The device includes a stylet having a blade for transecting and separating tissue. The device further includes a cannula for cutting a core of tissue and a garrote wire mechanism for cutting a transection of tissue transverse to the core cut by the cannula. The garrote wire is activated by a trigger mechanism which is locked out by a lockout feature within the device until the garrote wire has been advanced around the core of tissue cut by the cannula.

10 Claims, 12 Drawing Sheets

U.S. PATENT DOCUMENTS

| | | | | |
|---|---|---|---|---|
| 5,197,484 | A | 3/1993 | Kornberg et al. | 600/567 |
| 5,224,952 | A | 7/1993 | Deniega et al. | 606/184 |
| 5,240,011 | A | 8/1993 | Assa | 600/564 |
| 5,251,641 | A | 10/1993 | Xavier | 600/567 |
| 5,257,632 | A | 11/1993 | Turkel et al. | 600/567 |
| 5,271,380 | A | 12/1993 | Riek et al. | 600/104 |
| 5,271,414 | A | 12/1993 | Partika et al. | 600/567 |
| 5,290,294 | A | 3/1994 | Cox et al. | 606/108 |
| 5,331,972 | A | 7/1994 | Wadhwani et al. | 600/567 |
| 5,352,206 | A | 10/1994 | Cushieri et al. | 604/170.01 |
| 5,353,804 | A | 10/1994 | Kornberg et al. | 600/567 |
| 5,364,372 | A | 11/1994 | Danks et al. | 604/264 |
| 5,366,445 | A | 11/1994 | Haber et al. | 604/164.01 |
| 5,368,607 | A | 11/1994 | Freitas | 606/172 |
| 5,372,583 | A | 12/1994 | Roberts et al. | 604/506 |
| 5,372,588 | A | 12/1994 | Farley et al. | 604/170.01 |
| 5,385,572 | A | 1/1995 | Nobles et al. | 606/185 |
| 5,394,887 | A | 3/1995 | Haaga | 600/567 |
| 5,399,167 | A | 3/1995 | Deniega | 604/164.12 |
| 5,415,169 | A | 5/1995 | Siczek et al. | 600/427 |
| 5,415,182 | A | 5/1995 | Chin et al. | 600/567 |
| 5,419,138 | A | 5/1995 | Anderson et al. | 62/605 |
| 5,423,824 | A | 6/1995 | Akerfeldt et al. | 606/80 |
| 5,431,151 | A | 7/1995 | Riek et al. | 600/164.08 |
| 5,449,001 | A | 9/1995 | Terwilliger | 600/567 |
| 5,462,062 | A | 10/1995 | Rubinstein et al. | 600/567 |
| 5,472,426 | A | 12/1995 | Bonati et al. | 604/164.1 |
| 5,483,952 | A | 1/1996 | Aranyi | 600/131 |
| 5,487,392 | A | 1/1996 | Haaga | 600/566 |
| 5,488,958 | A | 2/1996 | Topel et al. | 600/567 |
| 5,511,556 | A | 4/1996 | DeSantis | 600/567 |
| 5,522,398 | A | 6/1996 | Goldberg et al. | 600/567 |
| 5,545,150 | A | 8/1996 | Danks et al. | 604/256 |
| 5,562,696 | A | 10/1996 | Nobles et al. | 606/185 |
| 5,573,008 | A | 11/1996 | Robinson et al. | 600/567 |
| 5,607,440 | A | 3/1997 | Danks et al. | 606/185 |
| 5,609,604 | A | 3/1997 | Schwemberger et al. | 606/185 |
| 5,620,456 | A | 4/1997 | Sauer et al. | 606/185 |
| 5,634,473 | A | 6/1997 | Goldberg et al. | 600/567 |
| 5,645,076 | A | 7/1997 | Yoon | 600/567 |
| 5,645,556 | A | 7/1997 | Yoon | 606/185 |
| 5,649,547 | A | 7/1997 | Ritchart et al. | 600/566 |
| 5,676,156 | A | 10/1997 | Yoon | 600/567 |
| 5,685,820 | A | 11/1997 | Riek et al. | 600/114 |
| 5,687,739 | A | 11/1997 | McPherson et al. | 600/567 |
| 5,709,671 | A | 1/1998 | Stephens et al. | 604/264 |
| 5,718,237 | A | 2/1998 | Haaga | 600/564 |
| 5,782,775 | A | 7/1998 | Milliman et al. | 600/567 |
| 5,795,308 | A | 8/1998 | Russin | 600/567 |
| 5,807,276 | A | 9/1998 | Russin | 600/567 |
| 5,810,806 | A | 9/1998 | Ritchart et al. | 606/45 |
| 5,810,826 | A | 9/1998 | Akerfeldt et al. | 606/80 |
| 5,817,034 | A | 10/1998 | Milliman et al. | 600/566 |
| 5,817,061 | A | 10/1998 | Goodwin et al. | 604/164.03 |
| 5,830,219 | A | | 11/1998 | Bird et al. | 606/130 |
| 5,857,982 | A | | 1/1999 | Milliman et al. | 600/567 |
| 5,872,775 | A | | 2/1999 | Saints et al. | 370/342 |
| 5,879,357 | A | | 3/1999 | Heaton et al. | 606/116 |
| 6,036,657 | A | | 3/2000 | Milliman et al. | 600/564 |
| 6,077,231 | A | * | 6/2000 | Milliman et al. | 600/567 |
| 6,080,113 | A | * | 6/2000 | Heneveld et al. | 600/564 |
| 6,080,114 | A | * | 6/2000 | Russin | 600/567 |
| 6,267,732 | B1 | * | 7/2001 | Heneveld et al. | 600/564 |
| 1,568,008 | A | | 12/1925 | Thomas | 30/113.3 |
| 1,609,456 | A | | 12/1926 | Boyle | 30/113.3 |
| 1,615,494 | A | | 1/1927 | Waring | 606/115 |
| 2,117,278 | A | | 5/1938 | Ainsworth | 30/113.1 |
| 2,919,692 | A | | 1/1960 | Ackerman | 600/567 |
| 3,470,867 | A | | 10/1969 | Goldsmith | 600/566 |
| 3,477,423 | A | | 11/1969 | Griffith | 600/567 |
| 3,605,721 | A | | 9/1971 | Hallac | 600/567 |
| 3,628,524 | A | | 12/1971 | Jamshidi | 600/567 |
| 3,850,158 | A | | 11/1974 | Elias et al. | 600/567 |
| 3,929,123 | A | | 12/1975 | Jamshidi | 600/567 |
| 4,010,737 | A | | 3/1977 | Vilaghy et al. | 600/567 |
| 4,099,518 | A | | 7/1978 | Baylis et al. | 30/113.1 |
| 4,174,715 | A | | 11/1979 | Hasson | 606/206 |
| 4,306,570 | A | | 12/1981 | Matthews | 600/567 |
| 4,448,205 | A | | 5/1984 | Stenkvist | 600/562 |
| 4,461,305 | A | | 7/1984 | Cibley | 600/567 |
| 4,535,773 | A | | 8/1985 | Yoon | 604/118 |
| 4,543,996 | A | | 10/1985 | Baron | 137/625.43 |
| 4,651,752 | A | | 3/1987 | Fuerst | 600/567 |
| 4,678,459 | A | | 7/1987 | Onik et al. | 604/22 |
| 4,776,346 | A | | 10/1988 | Beraha et al. | 600/567 |
| 4,785,826 | A | | 11/1988 | Ward | 600/567 |
| 4,817,631 | A | | 4/1989 | Pesch et al. | 600/566 |
| 4,838,280 | A | | 6/1989 | Haaga | 600/564 |
| 4,846,791 | A | | 7/1989 | Hattler et al. | 604/43 |
| 4,850,373 | A | | 7/1989 | Zatloukal et al. | 600/562 |
| 4,881,550 | A | | 11/1989 | Kothe | 600/565 |
| 4,926,877 | A | | 5/1990 | Bookwalter | 600/567 |
| 4,940,061 | A | | 7/1990 | Teriwilliger et al. | 600/567 |
| 4,958,625 | A | | 9/1990 | Bates et al. | 600/567 |
| 4,971,067 | A | | 11/1990 | Bolduc et al. | 600/564 |
| 4,989,614 | A | | 2/1991 | Dejter, Jr. et al. | 600/565 |
| 5,009,642 | A | | 4/1991 | Sahi | 604/158 |
| 5,036,860 | A | | 8/1991 | Leigh et al. | 600/567 |
| 5,057,082 | A | | 10/1991 | Burchette, Jr. | 604/164.06 |
| 5,078,142 | A | | 1/1992 | Siczek et al. | 600/407 |
| 5,111,828 | A | | 5/1992 | Kornberg et al. | 600/567 |
| 5,116,353 | A | | 5/1992 | Green | 606/184 |
| 5,127,419 | A | | 7/1992 | Kaldany | 600/567 |
| 5,133,360 | A | | 7/1992 | Spears | 600/567 |
| 5,148,813 | A | | 9/1992 | Bucalo | 600/567 |
| 5,183,052 | A | | 2/1993 | Terwilliger | 600/566 |
| 5,188,118 | A | | 2/1993 | Teriwilliger | 600/566 |

* cited by examiner

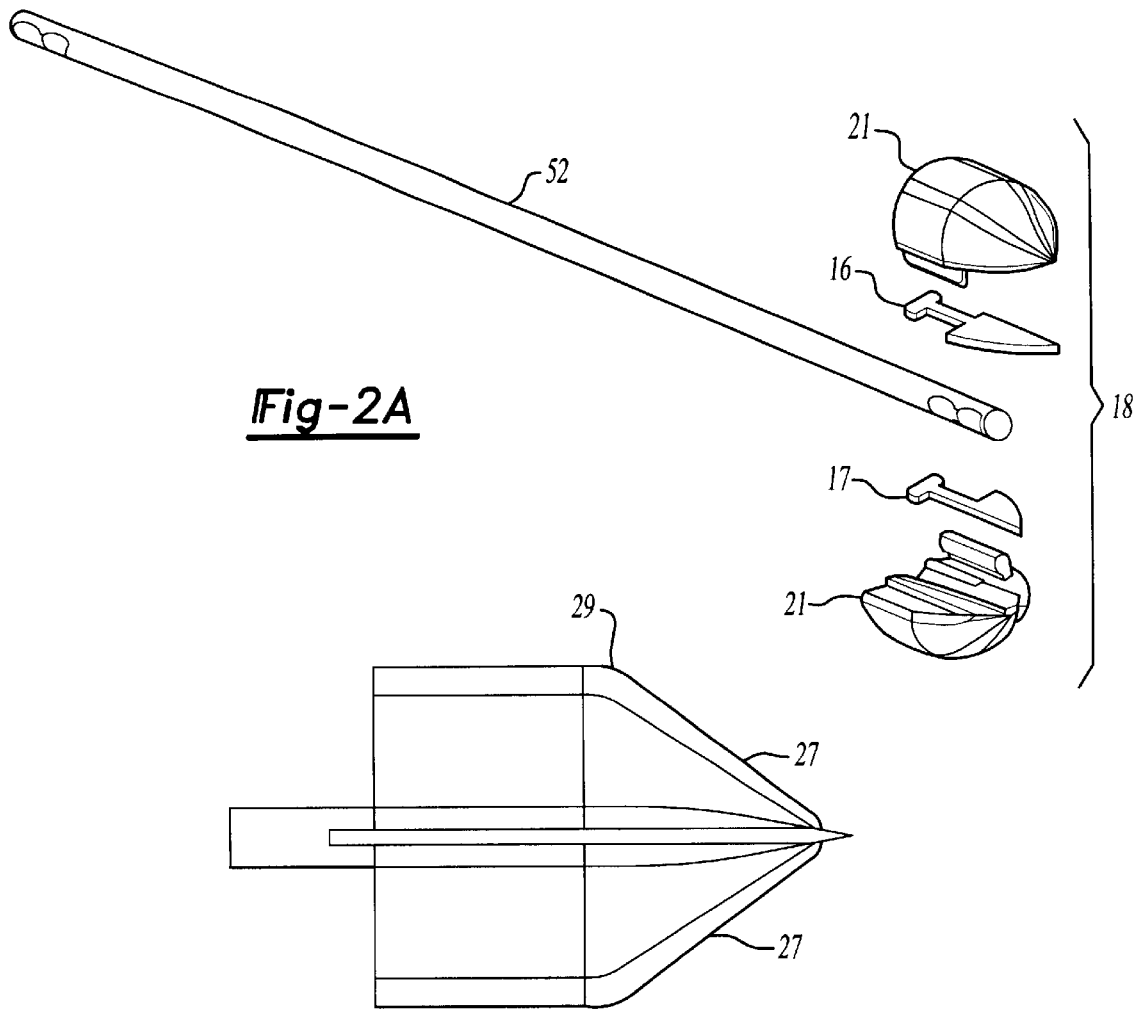
*Fig-2A*
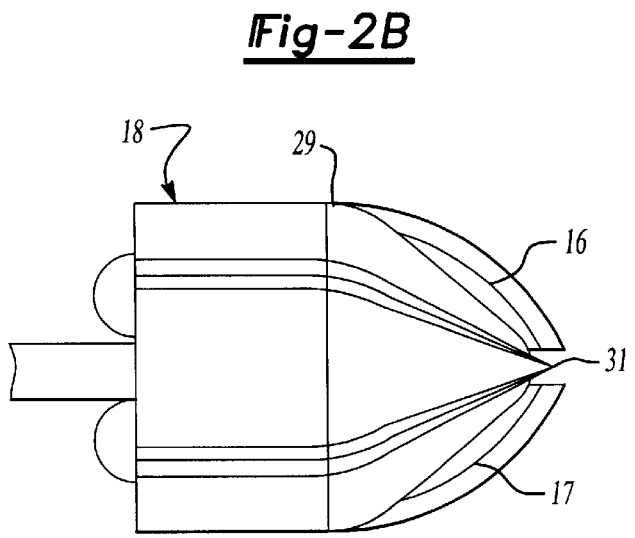
*Fig-2B*
*Fig-2C*

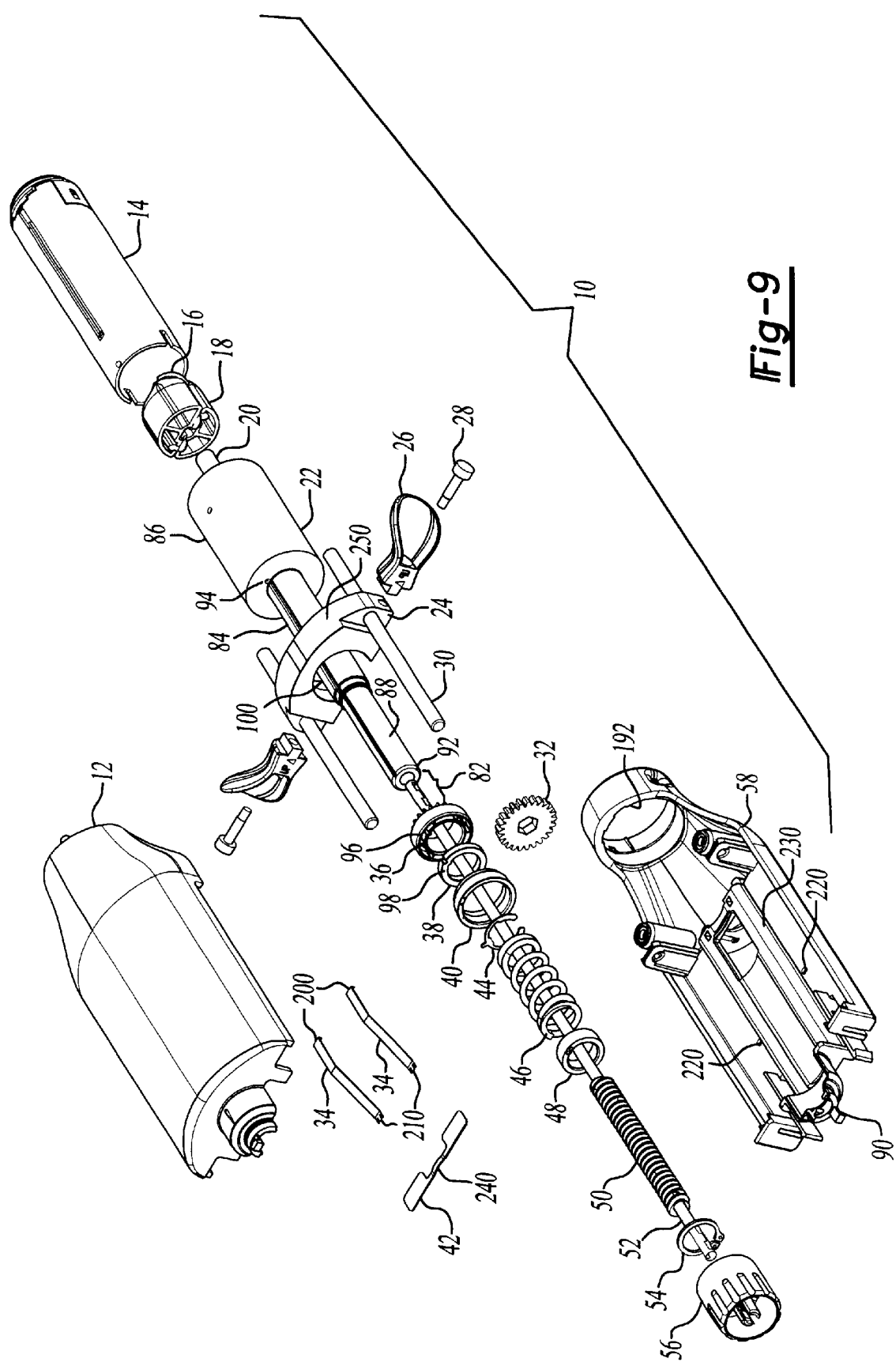

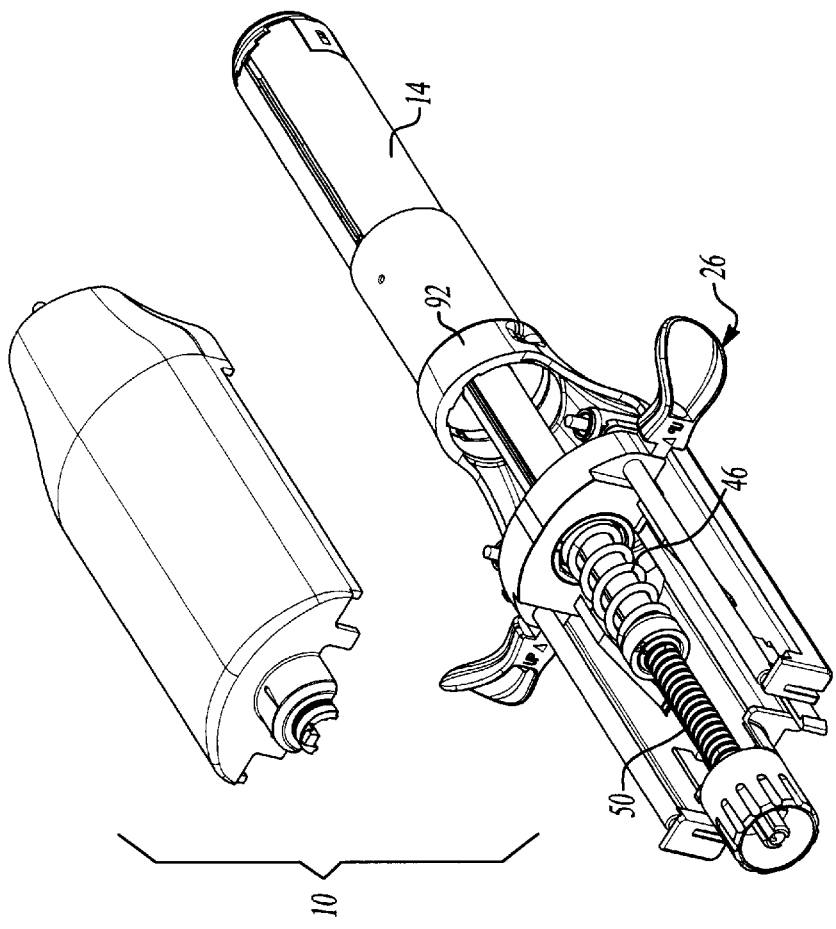
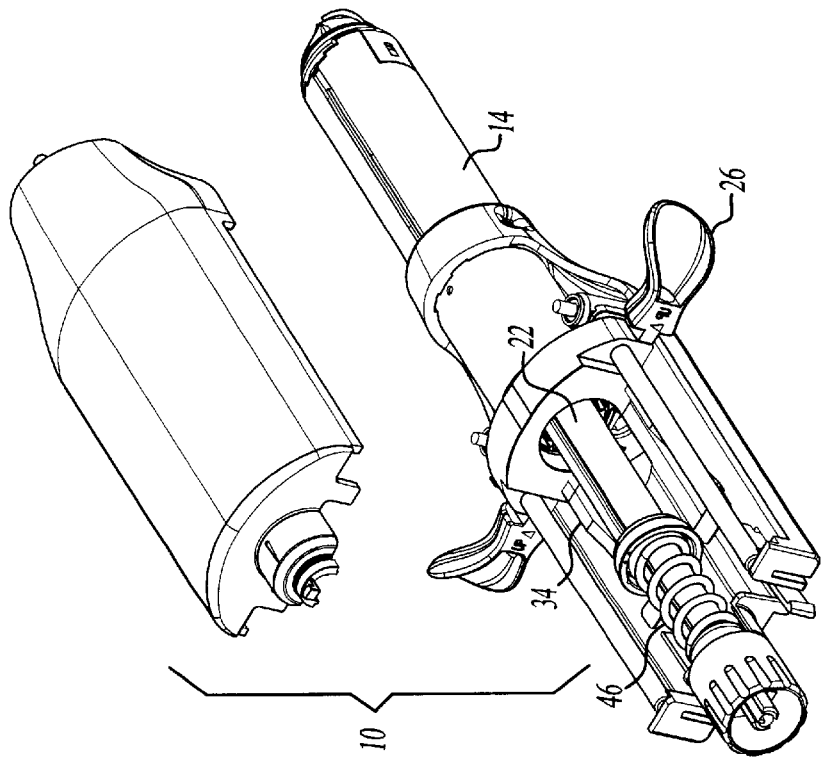

INCISIONAL BREAST BIOPSY DEVICE

This application is a continuation in part application of U.S. patent application Ser. No. 09/692,928 filed Oct. 20, 2000, now U.S. Pat. No. 6,383,145, which is a Continuation in Part Application of U.S. patent application Ser. No. 09/542,623 filed Apr. 04, 2000, now U.S. Pat. 6,267,732, which was a Continuation Application of patent application Ser. No. 09/151,439 filed Sep. 11, 1998, now U.S. Pat. No. 6,080,113 which claims benefit of U.S. Provisional Patent Application 60/058,691 filed Sep. 12, 1997.

BACKGROUND

This invention relates generally to surgical instruments and, more particularly, to a device for percutaneous incisional breast biopsy.

The early diagnosis of breast cancer through the use of mammography is very important for reducing the morbidity associated with breast cancer. Early diagnosis enables a physician to treat the breast cancer at a more manageable stage of development. Mammography is capable of detecting very small abnormalities in breast tissue. However, mammography usually cannot differentiate between malignant and benign lesions in the breast. Definitive determination of the status of a lesion often requires a histological examination of the suspect tissue.

One method for obtaining a tissue sample for histological examination is through a biopsy of part or all of the suspect tissue. There are a number of devices and methods for performing a biopsy of the breast. Generally, the procedure requires first placing a localization needle within or near the lesion. A guide wire contained within the localization needle is then deployed. The guide wire usually includes hooks that anchor one end of the guide wire in breast tissue near the lesion. Then a biopsy device that includes a cannula and a stylet located within the cannula is inserted over the localization needle and guide wire. The device is inserted through a small incision in the breast tissue near the entry point of the localization needle. The stylet bluntly separates breast tissue as the device is inserted over the guide wire toward the lesion. Advancement of the device is stopped once the tip of the stylet is within or near the lesion. Then, the cannula, which has a cutting surface at a leading edge, is advanced over the stylet and into the tissue thereby cutting a core of tissue. The cutting surface is advanced to a point beyond the end of the guide wire. Then, a second cutting surface, typically a wire garrote, is activated to perform a cut transverse to the core and to a longitudinal axis of the cannula creating a tissue sample. Then the needle, guide wire, and device are retracted from the breast with the tissue sample. The tissue sample is then histologically examined to determine whether the suspect tissue is malignant or benign.

The current biopsy devices have a number of disadvantages including that the device, localization needle, and guide wire are not manufactured as a single unit; also the devices generally do not have a means for insuring that the garrote wire is located past the end of the guide wire prior to deployment of the garrote. To determine whether the garrote is located past the end of the guide wire with a typical biopsy device, a radiographic check is required. Finally, the typical blunt stylet requires substantial force to insert and may cause trauma to the healthy tissue as it passes to the biopsy site.

Therefore, it is desirable to provide a biopsy device manufactured as an integrated unit having a localization needle and a guide wire. Additionally, it is desirable to provide a biopsy device having features to insure that the garrote wire is not deployed until it is past the end of the guide wire. It is also desirable to provide a stylet with cutting members to cleanly transect and separate breast tissue and minimize the damage to healthy tissue.

SUMMARY OF THE INVENTION

The present invention overcomes the problems with previous biopsy devices by providing a biopsy device which is manufactured with an integral localization needle and guide wire. In addition, the invention includes structure to insure that the garrote wire is not deployed until the garrote wire is beyond the end of the guide wire. Further, the stylet is provided a blade which transects tissue as the device is inserted to the biopsy site.

According to one aspect of the present invention, the device includes a cannula having a shaft with a cutting surface on one end of the shaft and the other end of the shaft in engagement with a drive assembly. Adjacent to the cutting surface of the cannula is a second cutting mechanism for making a cut transverse to a cut made by the shaft cutting surface. Located within the cannula shaft is a stylet. The stylet has a tip portion with a blade for transecting and separating tissue and a central chamber for permitting a localization needle to pass through the length of the stylet. The localization needle has an interior chamber permitting passage of a guide wire through the length of the localization needle. The device also includes a lock feature for preventing deployment of the second cutting mechanism until it is past the end of the guide wire.

According to a further aspect of the present invention, a method of removing suspect breast tissue with a breast biopsy device includes the steps of inserting a localization needle into tissue, advancing a hooked guide wire out of a distal end of the localization needle to anchor the biopsy device in the tissue in or near a lesion, advancing a stylet and cannula over the localization needle until the stylet is adjacent the lesion, advancing a cannula shaft cutting surface to cut a core of tissue, unlocking a trigger of a garrote when a cutting plane of the garrote has been advanced past a distal end of the guide wire, and moving the trigger to activate the garrote and make a cut transverse to the direction of advancement of the cannula shaft.

BRIEF DESCRIPTION OF THE DRAWINGS

FIG. 2A is an exploded view of a stylet of the present invention;

FIG. 2B is a side view of the stylet end.

FIG. 2C is a side view of the stylet end rotated 90° from the position in FIG. 2B.

FIG. 9 is an exploded view of the biopsy device with an upper and lower housing removed;

FIG. 10A is a top view of the biopsy device with the upper housing removed and the cannula shaft in a retracted position;

FIG. 10B is a top view of the biopsy device with the upper housing removed and the cannula shaft in an extended position;

DETAILED DESCRIPTION OF A PREFERRED EMBODIMENT

Figure 1:
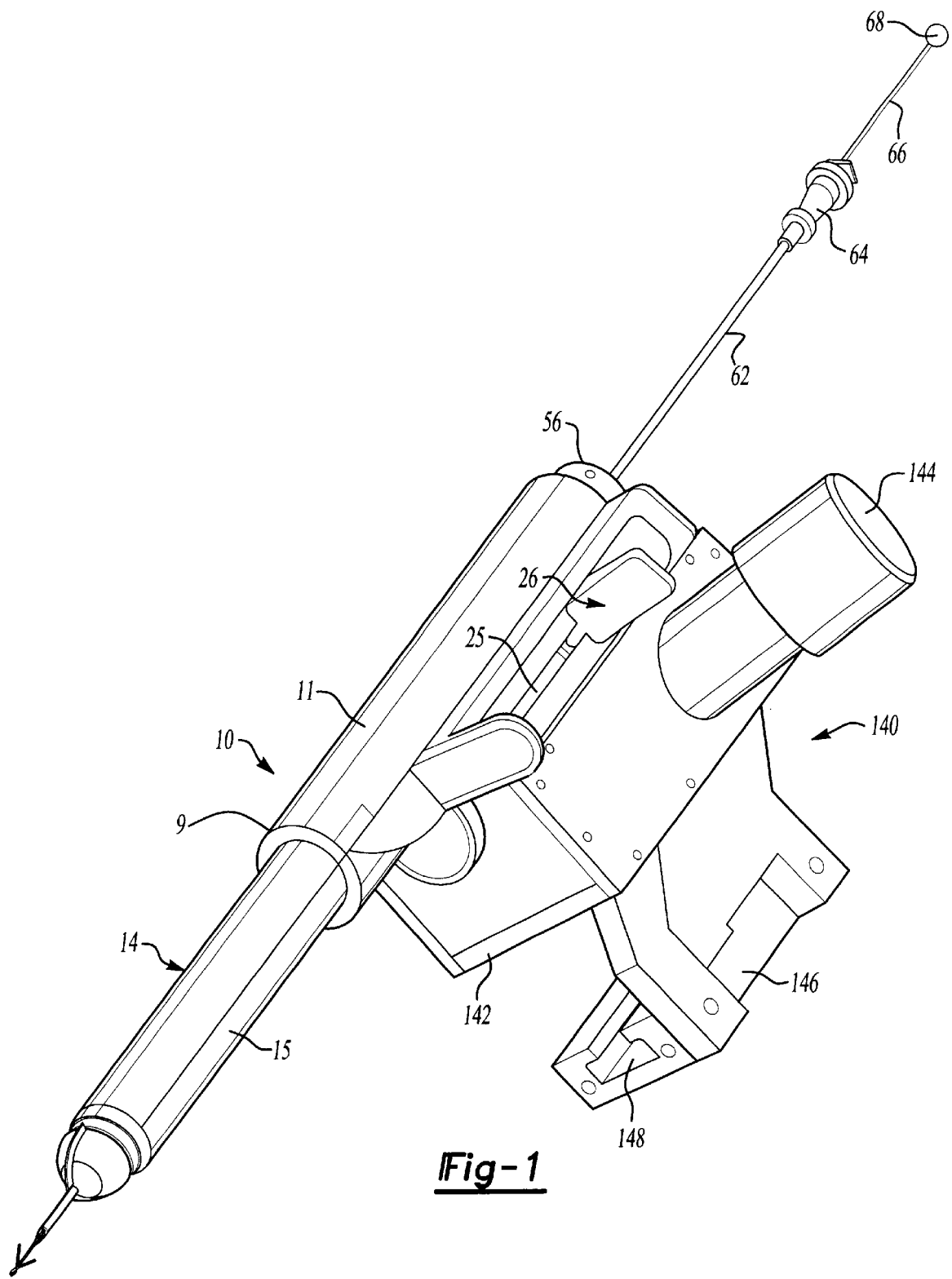
FIG. 1 is a perspective view of a biopsy device designed according to the invention mounted on an instrument holder.
Figure 3:
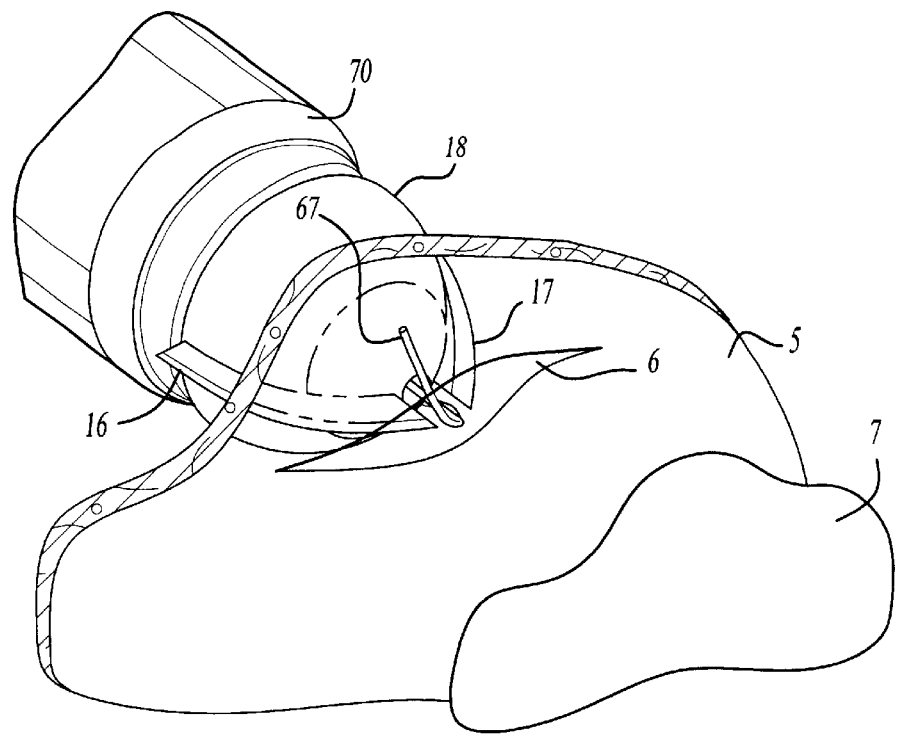
FIG. 3 is a perspective view of the stylet entering a tissue sample.
Figure 4:
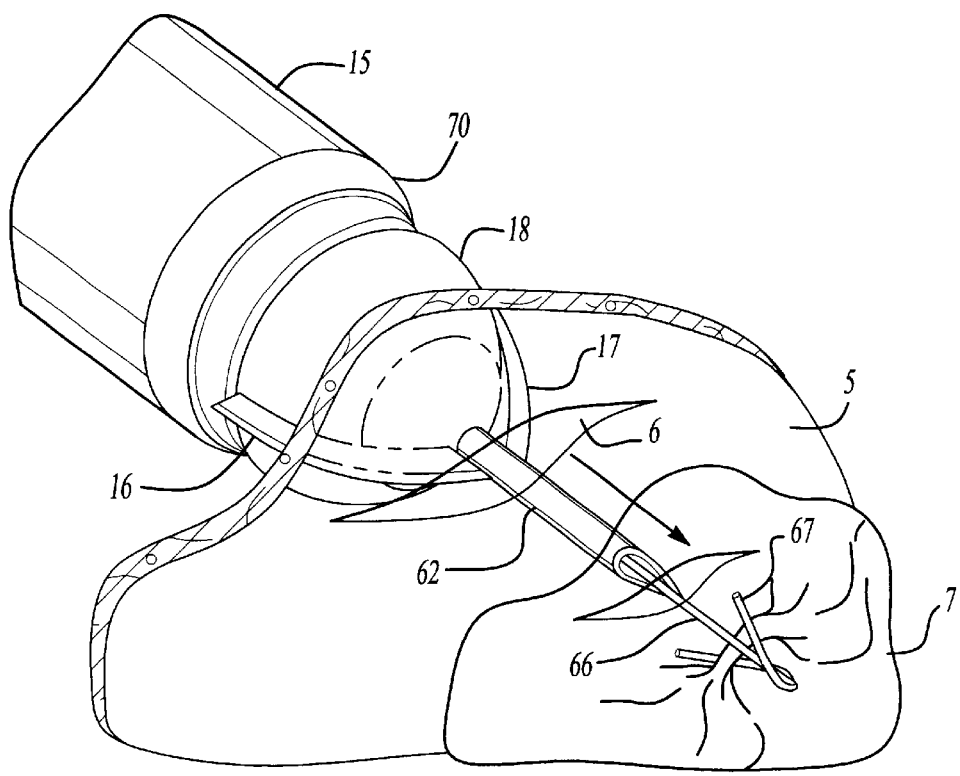
FIG. 4 is a perspective view of the stylet and a localization needle and a guide wire entering the tissue sample.
Figure 5:
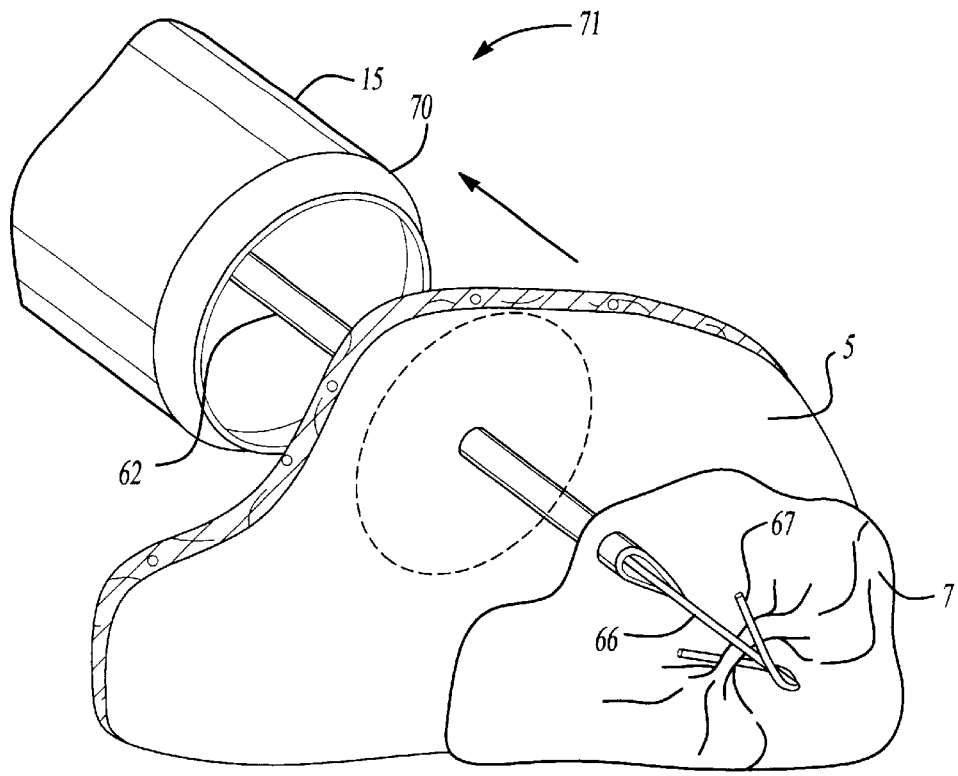
FIG. 5 is a perspective view of the localization needle and the guidewire inserted into the tissue sample and the stylet retracted within a cannula of the biopsy device.
Figure 6:
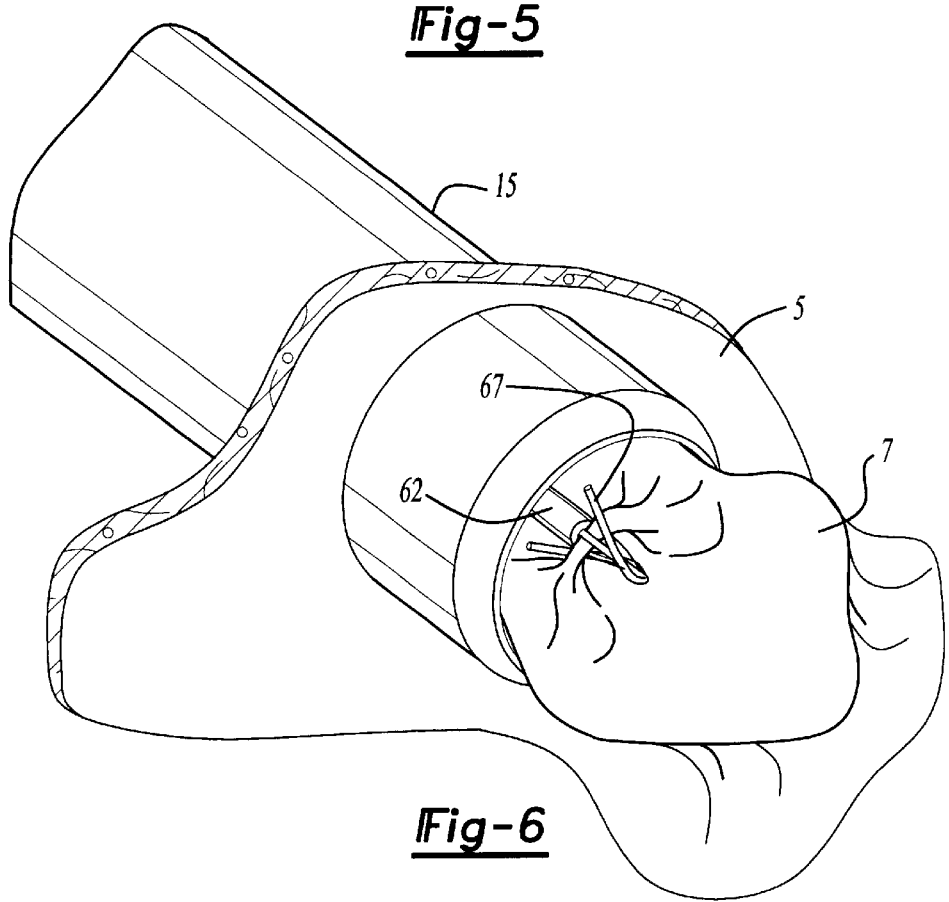
FIG. 6 is a perspective view of the cannula cored into the tissue sample.
Figure 7:
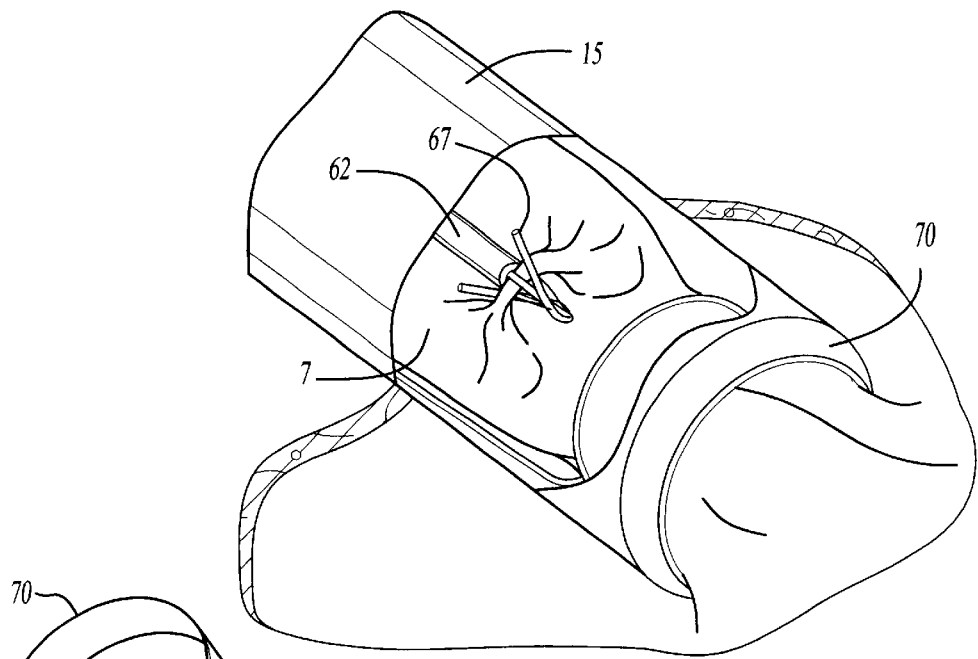
FIG. 7 is a perspective view of the cannula with a portion of the tissue pulled into the cannula by the guidewire.

Referring to the Figures wherein like numerals indicate like or corresponding parts throughout the several view, in FIG. 1 a biopsy device is shown generally at 10. The device 10 is shown mounted on an instrument holder 140. The instrument holder 140 includes a housing 142 and a rotation knob 144 mounted within the housing 142. A bracket 146 connects the housing 142 to a track 148. The track 148 can be fixed to a point along a rail (not shown) by a friction cam brake (not shown). The device 10 includes a housing 11 having a trigger slot 25. A trigger 26 extends through the trigger slot 25. A stylet retracting knob 56 is mounted adjacent a front end 9 of the housing 11 and connected to a stylet tube 52 (See FIGS. 1 and 2A). A localization needle 62 passes thought the stylet retracting knob 56 and through the stylet tube 52. A hub 64 is mounted on a proximal end of the localization needle 62.

A guide wire 66 is slidably received within the localization needle 62. A stop 68 is mounted on one end of the guide wire 66. A cannula 14 extends from a front end 9 of the housing 11. A stylet 18 is mounted on the stylet tube 52 and the stylet 18 extends beyond the end of the cannula 14 when the stylet tube 52 is extended and the cannula 14 is retracted.

In FIGS. 2A–2C the stylet 18 is shown in greater detail. The stylet 18 comprises a first blade 16 and a second blade 17 integrated between two halves of a stylet housing 21 onto an end of the stylet tube 52. The stylet housing 21 is preferably cone shaped with the first blade 16 and the second blade 17 exiting the cone. The stylet 18 transects, dilates, and separates tissue as the device 10 is inserted toward the biopsy site. In a preferred embodiment a leading edge 27 of the stylet housing 21 forms a forty five degree angle with the center axis 29 of the stylet housing 21. The leading edge 27 is then radiused at 31 into the body 33 of housing 21. Body portion 33 is generally parallel to the center axis 29. The first blade 16 and the second blade 17 are exposed in a curved fashion from an end 31' of the stylet housing 21 and extend to the center axis 29 of the stylet housing 21.

With reference to FIGS. 3–7, the biopsy device 10 is shown in various stages of deployment. First an incision 6 is made in the external surface of a breast tissue 5 adjacent a tissue lesion 7, the localization needle 62 is inserted into the lesion 7, and the guidewire 66 located within the localization needle 62 is deployed to anchor the biopsy device 10 in the lesion 7. Preferably, the guidewire 66 consists of a single wire with a barb 67 for marking, stabilizing, and holding the lesion 7. Alternatively, the guidewire 66 may consist of two or more wires and two or more barbs 67 for increasing the holding ability of the guidewire 66 in various densities of the breast tissue 5. The cannula 14 and the stylet 18 are then advanced over the localization needle 62 with the stylet 18 and blades 16, 17 transecting and separating the healthy breast tissue 5 with minimal trauma to the healthy tissue as the cannula 14 is inserted toward the lesion 7. The cannula 14 is then simultaneously advanced and rotated to core lesion 7. A cutting ring 70 is mounted within the cannula nose of the cannula 14 to provide the cutting action as the cannula 14 is extended. Once the core of lesion 7 has been cut a garrote wire cutting mechanism, as described below, is deployed to transect the tissue core creating an excised sample of tissue.

Figure 8:
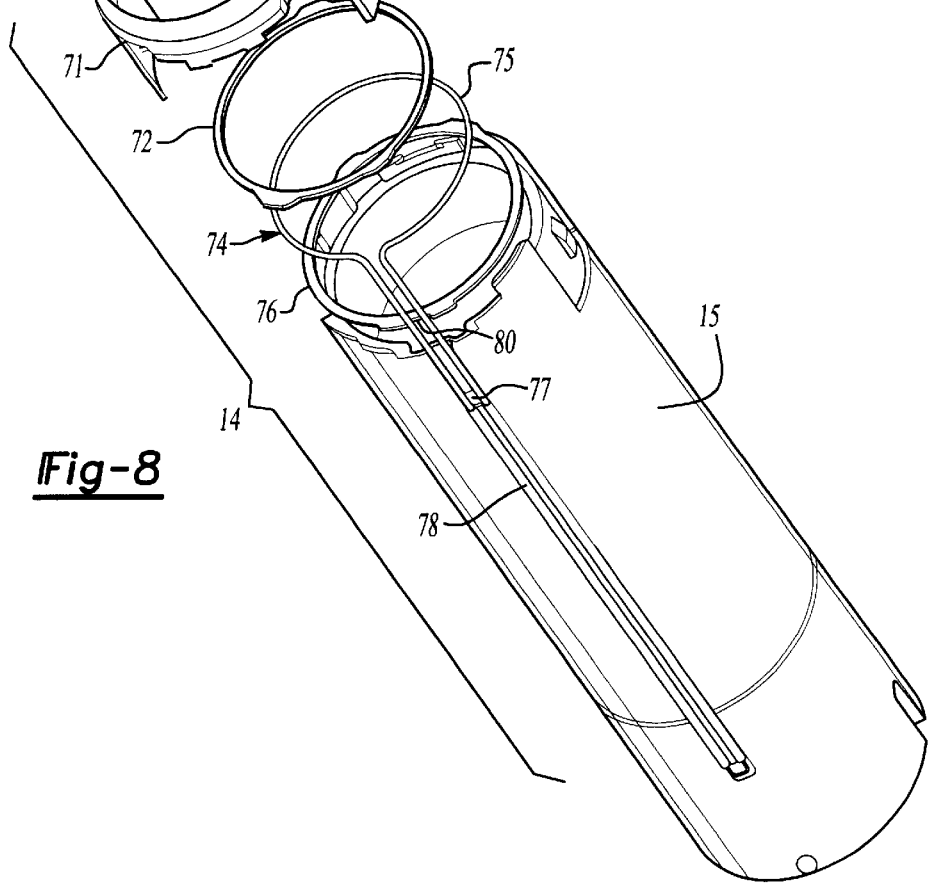
FIG. 8 is an exploded view of a cannula assembly.

FIG. 8 shows an exploded view of the cannula 14 and FIG. 9 shows an exploded view of the device 10. A garrote wire 74 having a looped section 75 that acts as a cutting surface is provided within the cannula 14. A center portion 77 of the garrote wire 74 extends from the looped section 75 into recessed garrote tubes 78 located on a side of the cannula 14. The garrote wire 74 exits the garrote tubes 78 and then proceeds into an opening 78a in the cannula 14. The garrote wire 74 then proceeds through an opening 94 in shaft 22 and continues through a hole 96 in a spline gear 36 and through a notch 98 in a stop ring 38. A first end of the garrote wire is attached to a trigger plunger 40. A second end of garrote wire 74 is attached to the spring plunger 40. A second end of garrote wire 74 is attached to the spring plunger 48. In the disclosed embodiment, an end cap 87 covers the end of cannula 14. The trigger plunger 40 is activated by movement of a trigger body 24 that is connected to trigger 26 and is used to activate the garrote wire 74 and cut the tissue plug in a direction transverse to the direction in which the cannula 14 was advanced. When the trigger 26 is pulled, the trigger body 24 engages the trigger plunger 40 causing trigger plunder 40 to move and pull one side of garrote wire 74. As plunger 40 moves, it engages and compresses spring 46 against spring plunger 48. Since spring plunger 48 can move with respect to trigger plunger 40, the side of the garrote wire 74 attached to spring plunger 48 can move in the opposite direction to the side of the garrote wire 74 attached to trigger plunger 40. In this way, there is a slight sawing action of the garrote wire 74.

The trigger 26 is provided with a locking mechanism, comprising a pair of trigger lock ramps 34 and a lock depressor 42, for preventing deployment of the garrote wire 74 prior to movement of a cutting plane of the garrote wire 74 past an end of the guidewire 66. The lock ramps 34 have a distal end 200 and a proximal end 210. The proximal end 210 is attached to the lower housing 58 at attachment points 220. The distal end 200 of lock ramps 34 is a free end and is adjacent a surface 250 of the trigger body 24 keeping the trigger body 24 from moving in a direction toward the lock ramps 34. In an undepressed state the distal end 200 is located at a height greater than that of the proximal end 210 relative to the housing 58. The lock depressor 42 is slidably mounted on a surface 230 of lower housing 58 and is connected to the trigger plunger 40 through a raised portion 240 of the lock depressor.

In application, as the cannula 14 is advanced to cut a core of tissue 5 and lesion 7 the trigger plunger 40 is advanced along the shaft 22 and thereby advances the lock depressor 42 along the lock ramps 34 depressing the distal end 200 of the lock ramps 34. This process continues until the cannula 14 has been advanced a predetermined distance to a point whereby the cutting plane of the garrote wire 74 contained within the cannula 14 has been advanced beyond the guide wire 66 and is thereby clear to make a cut. At this point, the distal end 200 of the lock ramps 34 are fully depressed by the lock depressor 42 and allow the trigger body 24 to move over the ramps 34 to deploy the garrote wire 74.

In a preferred embodiment of cannula 14 as shown in FIG. 8, the cannula 14 contains a distal disk blade 72 and a proximal disk blade 76 providing cutting surfaces in addition to cutting ring 70 to assist the garrote wire 74 in transecting the lesion 7. Alternatively, the cannula 14 could contain a plurality of additional blades. In this embodiment the garrote wire 74 exits the cannula 14 through a notch 80 in the proximal disk blade 76 and the looped section 75 of the garrote wire 74 is located between the proximal disk blade 76 and the distal disk blade 72.

In operation, the garrote wire 74 pulls the lesion 7 against the disk blades 72 and 76 to facilitate cutting of the lesion 7. Since the garrote is positioned between blades 72 and 76, the lesion 7 is pulled against the blades 72 and 76 which cuts into the lesion. By pulling the trigger 26, the garrote wire 74 cuts through one side of the lesion 7 as the blades 72 and 76 cut through the opposite side.

In FIG. 9, a drive assembly 82 is shown mounted within the housing 11. Housing 11 includes an upper housing 12 and a lower housing 58. The drive assembly 82 includes a cylindrical shaft 22 with a proximal end 88 and a distal end 86. The distal end 86 of shaft 22 has a larger diameter than the proximal end 88. A portion of shaft 22 beginning at the proximal end 88 contains a spline 84 for mounting the spline gear 36. A screw base 90 is formed within the lower housing 58. A lead screw 50 is mounted to the screw base 90 and extends into an internally threaded portion of the proximal end 88 of the shaft 22, thereby supporting the proximal end 88 of the shaft 22. A shaft housing 192 is formed in an end of lower housing 58 and supports the distal end 86 of shaft 22. A drive gear 32 is mounted within the lower housing 58 and engages the spline gear 36. In use, the drive gear 32 is driven by rotation of the rotation knob 144 and in turn drive gear 32 rotates the spline gear 36. Rotation of the spline gear 36 advances the shaft 22 down the lead screw 50. Movement of the shaft 22 advances and rotates the cannula 14 into the tissue which cuts a core of tissue as the cutting ring 70 rotates and advances. A compression spring 46 is mounted around the shaft 22 and is held at one end by a clip 44 and at another end by a spring plunger 48. Located between the clip 44 and the spline gear 36 are the stop ring 38 and the trigger plunger 40. The triggers 26 are connected to the trigger body 24 by a pair of shoulder screws 28. The trigger body 24 rides on two trigger rods 30 mounted in lower housing 58 and contains an opening 100 which allows the trigger body 24 to engage the trigger plunger 40. Both the trigger body 24 and the trigger plunger 40 ride over the shaft 22 during activation of the trigger 26.

In FIGS. 10A–10B, the cannula 14 and the lead screw 50 are shown, respectively, before and after coring of the tissue. FIG. 10A shows the cannula 14 in a fully retracted position with the lead screw 50 completely inside of the threaded portion of shaft 22. As the spline gear 36 is rotated the cannula 14 is advanced into the tissue 5. FIG. 10B shows the cannula 14 and the lead screw 50 fully extended. The length of travel of the cannula 14 is limited by the length of the lead screw 50 and the length of the shaft 22. It is possible in the current invention to have different sizes of biopsy devices 10 including different diameters and lengths of the cannula 14, corresponding shaft 22, and the lead screw 50 to provide different diameters and length core samples. In FIGS. 10A–10B the trigger 26 is shown in a locked position forward of a pair of trigger lock ramps 34.

Figure 10D:
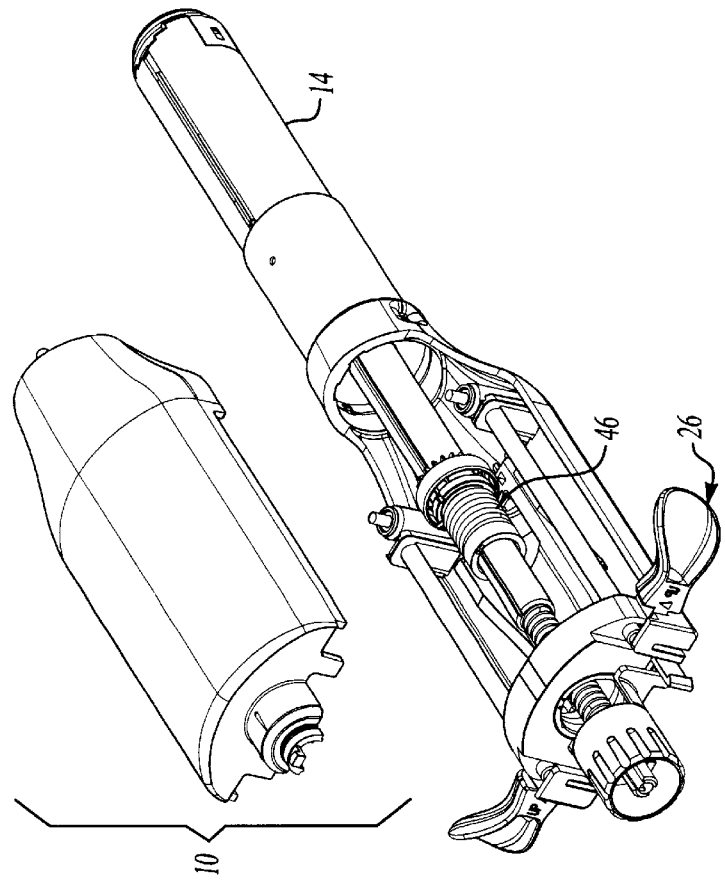
FIG. 10D is a top view of the biopsy device with the upper housing removed showing full deployment of the trigger.
Figure 10C:
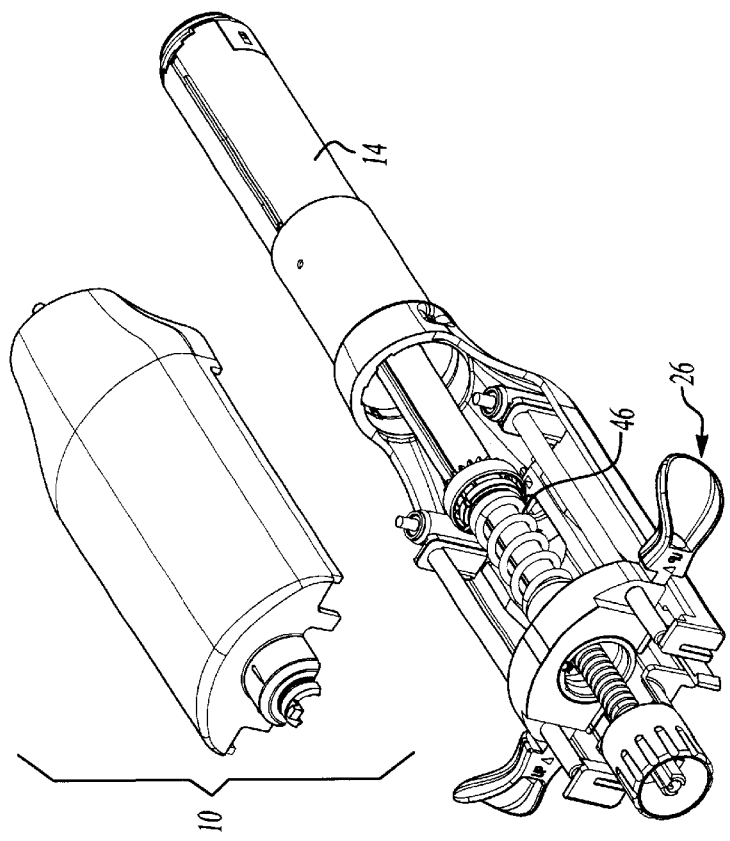
FIG. 10C is a top view of the biopsy device with the upper housing removed and the trigger partially deployed.
Figure 10F:
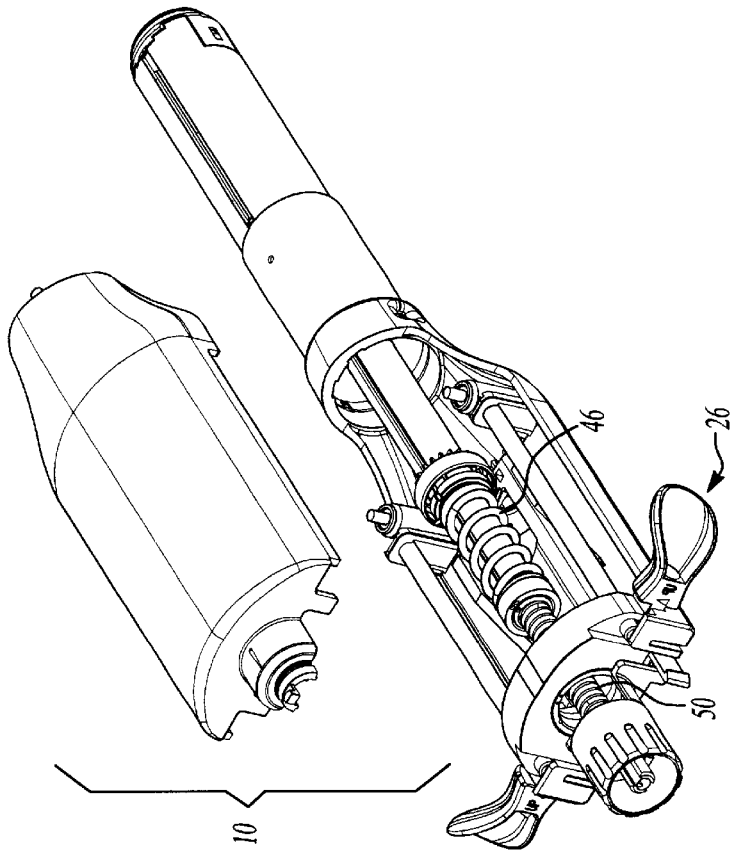
FIG. 10F is a top view of the biopsy device with the upper housing removed and shown after completion of a transection of the tissue sample.
Figure 10E:
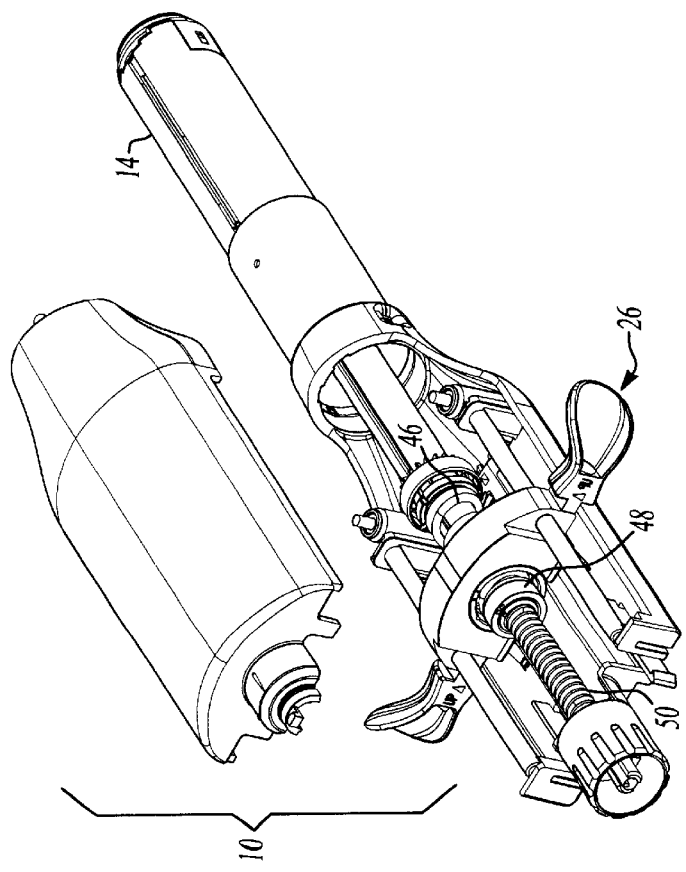
FIG. 10E is a top view of the biopsy device with the upper housing removed showing resetting of the trigger.

In FIGS. 10C–10F, the device 10 is shown in the following stages: partial deployment of the trigger 26, FIG. 10C; full deployment of the trigger 26, FIG. 10D; during return of the trigger 26, FIG. 10E; and after complete transection of the tissue lesion 7 has taken place, FIG. 10F. To deploy the garrote wire 74 a lock depressor 42 (Shown in FIG. 9) depresses the trigger lock ramps 34 allowing the trigger body 24 to ride over and down the ramps 34. When the triggers 26 are activated, the trigger body 24 slides along the pair of trigger rods 30. The trigger body 24 interfaces with the trigger plunger 40 pushing the trigger plunger 40 down the shaft 22, thereby pulling the ends of the garrote wire 74, which is attached to the trigger plunger 40 and spring plunger 48, and closing the looped section 75 (not shown) of the garrote wire 74 around the tissue lesion 7. In FIG. 10C, the trigger 26 is only partially deployed and the spring 46 is expanded. In FIG. 10D, the trigger 26 is fully deployed and the spring 46 is then compressed. As shown in FIGS. 10D and 10E, the spring 46 keeps tension on the spring plunger 48 while the trigger 26 is reset for another pull on the garrote wire 74. In this embodiment the trigger 26 may be oscillated an unlimited number of times until the garrote wire 74 successfully makes the transection. Multiple oscillations of the trigger 26 enable the actions of the garrote wire 74 to act as a saw on the tissue for cutting difficult tissue. In an alternative embodiment of device 10, the spring 46, the stop ring 38, and the spring plunger 48, present in the device 10 shown in FIG. 9, may be absent from the device 10 allowing for only a one time activation of the trigger 26 and the garrote wire 74. This is accomplished by attaching both ends of the garrote wire 74 to the trigger plunger 40.

FIG. 10F shows the device 10 after a completed tissue transection. After the transection is complete the cannula 14 and the device 10 are retracted from the biopsy site to retrieve the tissue sample present within the cannula 14.

Figure 11:
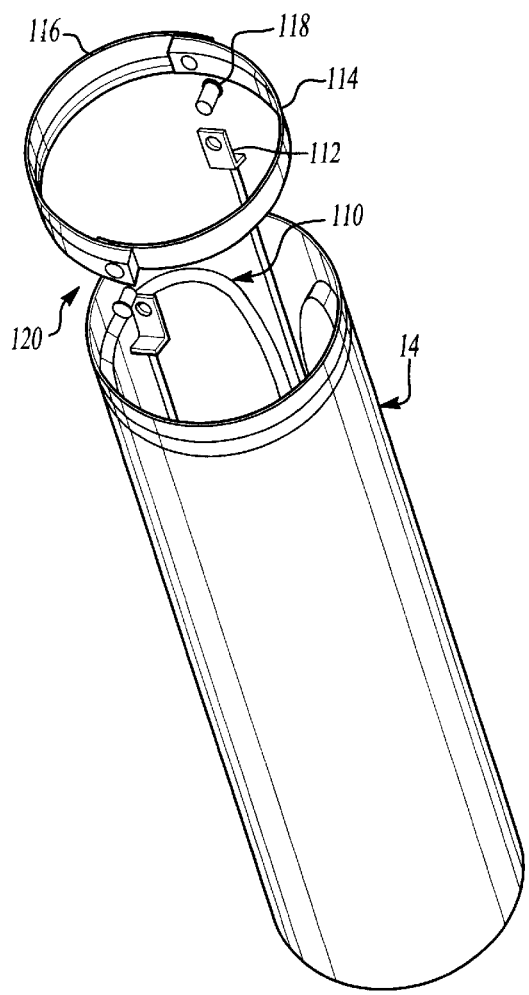
FIG. 11 is an exploded view of an alternative cutting mechanism housed within the cannula.

FIG. 11 shows an alternative embodiment of a cutting mechanism 120 located within the cannula 14 in place of the garrote wire 74. The cutting mechanism 120 comprises a semi-circular inner blade 114 and a semi-circular outer blade 116 connected by a pair of pivot pins 118 which are supported by a pair of actuation rods 112. Alternatively the inner blade 114 and the outer blade 116 may be elliptical in shape. The inner blade 114 and the outer blade 116 are supported on a pair of curved cam surfaces 110 that are mounted or molded internally within cannula 14. In operation, the cutting mechanism 120 is actuated by pulling the actuation rods 112, thereby forcing the inner blade 114 and the outer blade 116 to follow the cam surface 110 and pivot in an upward direction toward each other. This actuation is made after the cannula 14 is advanced to a desired location. Alternatively, the cutting mechanism 120 may also be used to core a section of tissue 5 and lesion 7 by applying a longitudinal and/or rotational force to the cannula 14 attached to the inner blade 114 and the outer blade 116 in their un-pivoted states.

Figure 12A:
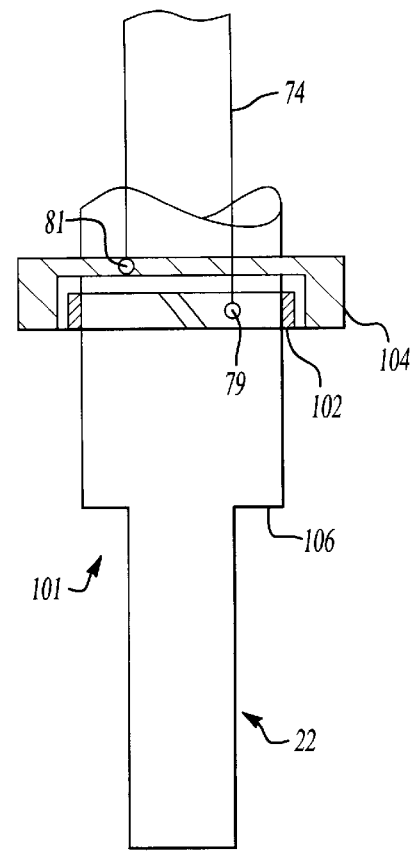
FIGS. 12A–12B are side views of an alternative garrote wire mechanism including an inner and outer sleeve shown prior to and during deployment, respectively.
Figure 12B:
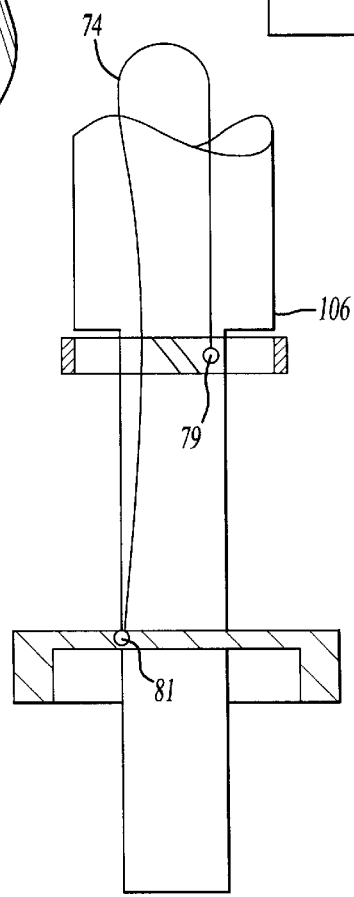

In FIGS. 12A–12B an alternative sleeve mechanism for activating the garrote wire 74 of the biopsy device 10 is shown generally at 100'. The sleeve mechanism 100' comprises a split ring inner sleeve 102 and an outer sleeve 104 mounted around the shaft 22 of the biopsy device 10. The first end 79 of garrote wire 74 is connected to the inner sleeve 102 and the second end 81 of garrote wire 74 is connected to the outer sleeve 104. In FIG. 12A the mechanism 100' is shown in a pre-deployment state with the inner sleeve 102 housed within the outer sleeve 104 and in an expanded state. In use, the garrote wire 74 is activated by pulling the trigger 26 which first pulls down on both the inner sleeve 102 and the outer sleeve 104 simultaneously thereby placing an even force on both the first and second ends, 79,81, of the garrote wire 74. As the inner and outer sleeves, 102, 104, are pulled past a shoulder 106 of the shaft 22, as shown in FIG. 12B the inner sleeve 102 allows the outer sleeve 104 to be pulled over the inner sleeve 102. The inner sleeve 102 is allowed to contract after it clears shoulder 106. The inner sleeve 102 is now pulled in an opposite direction against the shoulder 106. Alternatively, both the inner and outer sleeves 102, 104 can be replaced by a single sleeve resulting in an even pull on the garrote wire 74. The need to increase the force on the garrote wire 74 to increase the transection force is determined by the density of the lesion 7 and tissue 5 encountered during the transection. The density of the lesion 7 and the tissue 5 may change as the transection is made through additional layers of tissue, and thus the device as shown in FIGS. 12A–12B allows for changes in the force applied to the garrote wire 74 during the transection process.

Figure 13A:
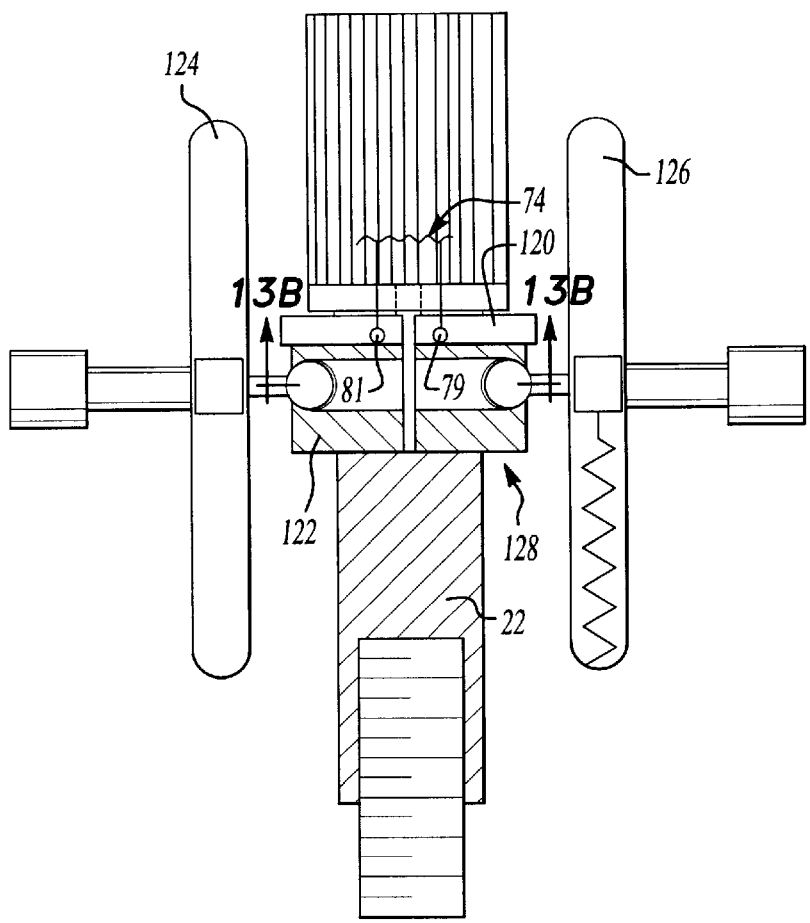
FIGS. 13A–13B are side and cross-sectional views, respectively, of an alternative garrote wire mechanism including a first and a second independent sleeve.
Figure 13B:
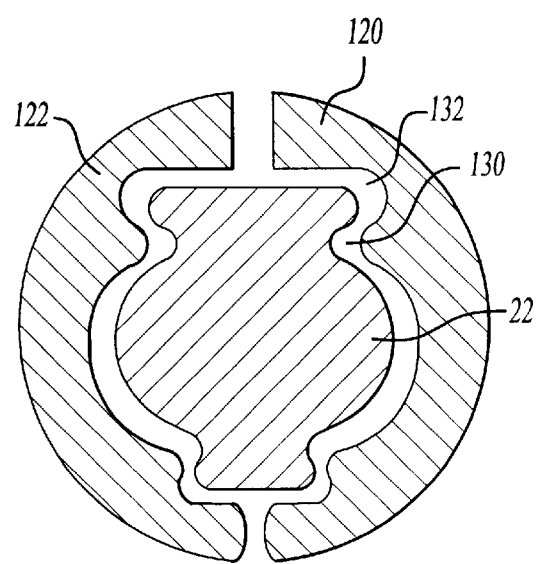

In FIGS. 13A–13B an alternative split sleeve garrote wire mechanism of the biopsy device 10 is shown generally at 128. As shown in FIG. 13A, the split sleeve mechanism 128 comprises a first sleeve half 120' and a second sleeve half 122 mounted around the shaft 22 of the biopsy device 10. As shown in FIG. 13B, the first and second sleeve halves 120', 122 are mounted on to the shaft 22 in such a way that they are independently movable up and down the shaft 22, but are not independently rotatable on the shaft 22. An outside geometry 130 of the shaft 22 and a corresponding inside geometry 132 of the first and second sleeve halves 120', 122 prevent the first and second sleeve halves 120', 122 from rotating-around the shaft 22. The geometries 130, 132 may be any non-circular shape thereby preventing the first and second sleeve halves 120', 122 from rotating around the shaft 22.

In FIG. 13A the first end 79 of the garrote wire 74 is connected to the first sleeve half 120 and the second end 81 of the garrote wire 74 is connected to the second sleeve half 122 such that the first and second ends 79, 81 of the garrote wire 74 move when the first and second sleeve halves 120,122 move up and down the shaft 22. Connected to the first sleeve half 120 is a first lever 126 and connected to the second sleeve half 122 is a second lever 124 for moving the sleeve halves 120, 122 up and down the shaft 22. In operation, the first and second levers 126, 124 may be moved simultaneously pulling equally on the first end 79 and the second end 81 of the garrote wire 74. The first and second levers 126, 124 may also be moved independently creating different forces on the first end 79 and the second end 81 of the garrote wire 74. The first and second lever 126, 124 may also be alternatively moved together and independently to create an alternating force on the first end 79 and the second end 81 of the garrote wire 74. The different movements of the first and second levers 126, 124 may be made at different times during the transection of the tissue by the garrote wire 74 depending on the density of the tissue being cut and the force needed to successfully transect that tissue. Thus, the mechanism provides for oscillatory movement of the garrote wire 74, creating a sawing action.

Figure 14:
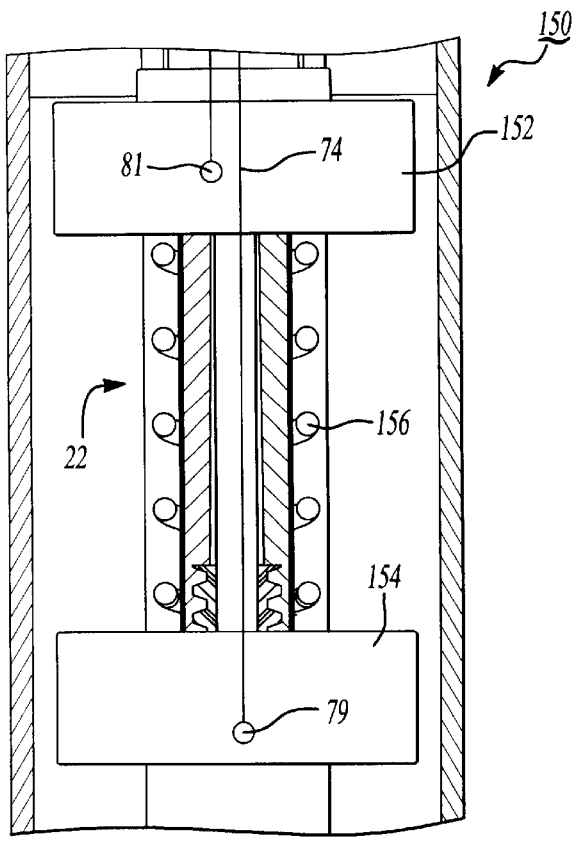
FIG. 14 is a cross-sectional view of an alternative garrote wire mechanism including a first and second sleeve interconnected by a spring.

In FIG. 14 an alternative sleeve/spring garrote wire activation mechanism of the biopsy device 10 is shown generally at 150. The activation mechanism 150 comprises a first sleeve 154 and a second sleeve 152 mounted around shaft 22. Connected to the first sleeve 154 is the first end 79 of the garrote wire 74. Connected the second sleeve 152 is the second end 81 of the garrote wire 74. The first sleeve 154 is connected to the second sleeve 152 by a spring 156. Alternatively, the spring 156 may consist of a plurality of springs (not shown). In use, the second sleeve 152 is moved down the shaft 22 by a lever mechanism similar to the first and second levers shown in FIG. 13, thereby pulling on both the second end 81 of the garrote wire 74 and pulling on the first sleeve 154 through the connection of the spring 156. The movement on the first sleeve 154 and the corresponding connected first end 81 of the garrote wire 74 is dependent on a spring force constant of the spring 156. The lower the spring force constant of the spring 156 the less initial movement of the first sleeve 154 takes place due to stretch of the spring 156. As the spring 156 is stretched to its limit the movement of the first sleeve 154 becomes equal to a rate of movement of the second sleeve 152. Alternatively, if the spring force constant of the spring 156 is set sufficiently high the first and second sleeves, 154, 152 may move together initially until the spring force is overcome by the lesion 7 resistance to the cutting action of garrote wire 74 acting on the second sleeve 152 and then the first and second sleeves 154, 152 may move independently while the spring 156 is stretched and then finally the first and second sleeves 154,152 may move together again after the spring 156 has been stretched completely. Alternatively the spring 156 may initially be placed in compression by initially pulling on the first sleeve 154 thereby compressing the spring 156 between the first sleeve 154 and the second sleeve 152. This alternative creates an initial force less than the spring force on the first end 81 of the garrote wire 74 until the spring 156 compresses and then both the first and second ends 81, 79 of the garrote wire 74 move together as both the first and second sleeves, 154, 152 are moved together down the shaft 22. The activation mechanism 150 creates an oscillating action allowing for differing forces to be applied to the garrote wire 74 during the transection of different density tissue.

Figure 15:
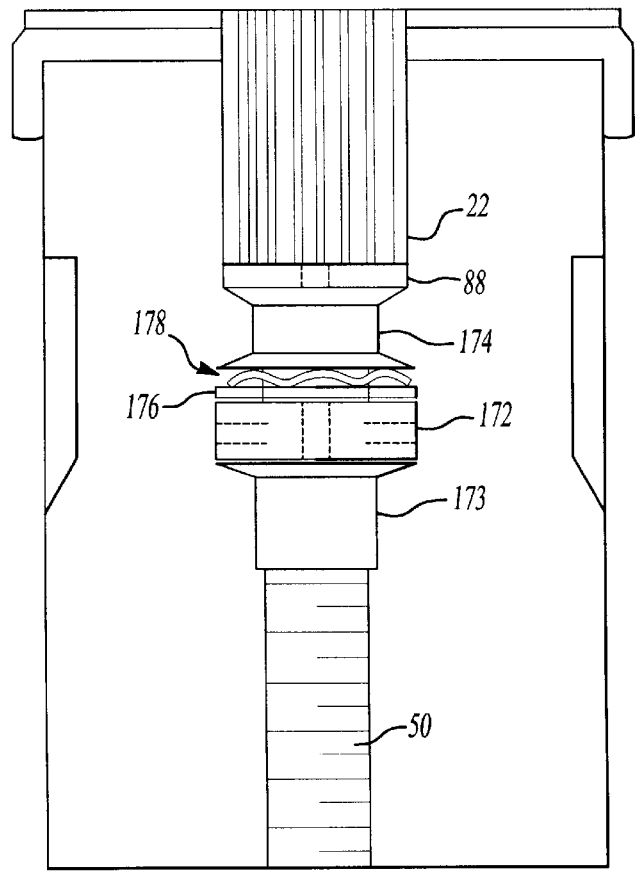
FIG. 15 is a perspective view of an alternative garrote wire mechanism comprising a wire spool mechanism.

In FIG. 15 an alternative spool mechanism for activating the garrote wire 74 is shown generally at 170. The mechanism 170 includes a garrote wire feed out spool 174, a washer 178, a snap ring 176, a guide collar 172, and a take up spool 173, mounted on the lead screw 50 at the proximal end 88 of the shaft 22. The first end 79 and a length of the garrote wire 74 (not shown) is coiled around the feed out spool 174 and is released from the feed out spool 174 as the second end 81 of the garrote wire 74 connected to the take up spool 173 is pulled and wrapped around the take up spool 173 when the take up spool 173 is rotated by the lead screw 50. The take up spool 173 is rotated thereby pulling the garrote wire 74 through the lesion 7 surrounded by the looped section 75 of the garrote wire 74 thereby creating a saw like action on the lesion 7. The take up spool 173 is rotated until a successful transection of the lesion 7 has been completed.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

We claim:

1. A biopsy device, comprising:

cannula having a shaft;

a retractable stylet having a tip containing at least one blade and a central passage;

a localization needle disposed within the central passage;

a drive mechanism for simultaneously rotating said cannula and moving said cannula in a direction parallel to a longitudinal axis of said cannula;

a garrote coupled to the cannula and being adapted to perform a cut traverse to said longitudinal axis of said cannula;

a trigger for deploying said garrote and for preventing deployment of said garrote prior to movement of said cannula a predetermined distance; and, a spring mounted around said drive mechanism for applying resistance against said garrote.

2. A biopsy device, comprising:

cannula having a shaft and a cutting ring;

a retractable stylet having a tip containing at least one blade and a central passage;

a localization needle disposed within the central passage;

a drive mechanism for simultaneously rotating said cannula and moving said cannula in a direction parallel to a longitudinal axis of said cannula;

a garrote coupled to-the cannula adjacent the cutting ring and being adapted to perform a cut traverse to said longitudinal axis of said cannula;

a trigger for deploying said garrote and for preventing deployment of said garrote prior to movement of said cannula a predetermined distance; and, a pair of disk blades mounted to the cannula.

3. A biopsy device, comprising:

a cannula having a shaft and a cutting ring;

a retractable stylet having a tip containing at least one blade and a central passage;

a localization needle disposed within the central passage;

a drive mechanism for simultaneously rotating said cannula and moving said cannula in a direction parallel to a longitudinal axis of said cannula;

a garrote coupled to the cannula adjacent the cutting ring and being adapted to perform a cut traverse to said longitudinal axis of said cannula;

a trigger for deploying said garrote and for preventing deployment of said garrote prior to movement of said cannula a predetermined distance; and, a distal disk blade and a proximal disk blade, the proximal disk blade containing a notch for receiving said garrote as the garrote exits the cannula to form a cutting surface.

4. The biopsy device, as set forth in claim 3, wherein the trigger includes a locking mechanism having a locked position and an unlocked position, wherein the trigger abuts a plurality of ramps that are depressed by a lock depressor during advancement of said cannula when the locking mechanism is in the locked position.

5. The biopsy device, as set forth in claim 4, wherein the trigger can be retracted to deploy the garrote when the locking mechanism is in the unlocked position.

6. A biopsy device, comprising:

a cannula having a shaft;

a retractable stylet having a tip containing at least one blade and a central passage;

a localization needle disposed within the central passage;

a drive mechanism for simultaneously rotating said cannula and moving said cannula in a direction parallel to a longitudinal axis of said cannula;

a garrote coupled to the cannula and being adapted to perform a cut traverse to said longitudinal axis of said cannula;

a trigger for deploying said garrote and for preventing deployment of said garrote prior to movement of said cannula a predetermined distance;

a localization needle having a guide wire mounted within said needle, wherein the trigger includes a locking mechanism for preventing deployment of the garrote until a cutting plane of the garrote is beyond an end of said guide wire.

7. The biopsy device, as set forth in claim 6, wherein the guide wire includes a barb for anchoring one end of said guide wire in a tissue sample.

8. A biopsy device, comprising:

a cannula having a shaft;

a retractable stylet having a tip containing at least one blade and a central passage;

a localization needle disposed within the central passage;

a drive mechanism for simultaneously rotating said cannula and moving said cannula in a direction parallel to a longitudinal axis of said cannula;

a garrote coupled to the cannula and being adapted to perform a cut traverse to said longitudinal axis of said cannula;

a trigger for deploying said garrote and for preventing deployment of said garrote prior to movement of said cannula a predetermined distance;

a trigger plunger coupled to the trigger, one end of the garrote being connected to the trigger plunger; and a spring plunger coupled to the trigger plunger via a spring, another end of the garrote being connected to the spring plunger.

9. The biopsy device, as set forth in claim 8, wherein the trigger includes a locking mechanism having a locked position and an unlocked position, wherein the trigger abuts a plurality of ramps that are depressed by a lock depressor during advancement of said cannula when the locking mechanism is in the locked position.

10. A biopsy device, comprising:

a cannula having a shaft and at least one disk blade mounted within the shaft;

a retractable stylet having a tip containing at least one blade and a central passage;

a drive mechanism for advancing the cannula in a direction parallel to a longitudinal axis of the cannula;

a garrote coupled to the cannula, the garrote and the disk blade being adapted to perform a cut traverse to said longitudinal axis of said cannula;

a trigger plunger connected to one end of the garrote; and, a spring plunger coupled to the trigger plunger via a spring, another end of the garrote being connected to the spring plunger.

* * * * *